(12) United States Patent
Mizoguchi et al.

(10) Patent No.: US 11,805,977 B2
(45) Date of Patent: Nov. 7, 2023

(54) ENDOSCOPE SYSTEM AND CONTROL METHOD FOR ENDOSCOPE SYSTEM

(71) Applicant: OLYMPUS CORPORATION, Tokyo (JP)

(72) Inventors: Masakazu Mizoguchi, Hachioji (JP); Toshiaki Watanabe, Hino (JP); Satoshi Takekoshi, Hachioji (JP); Susumu Aono, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 715 days.

(21) Appl. No.: 16/907,499

(22) Filed: Jun. 22, 2020

(65) Prior Publication Data

US 2020/0315439 A1 Oct. 8, 2020

Related U.S. Application Data

(63) Continuation of application No. PCT/JP2018/038315, filed on Oct. 15, 2018.

(30) Foreign Application Priority Data

Dec. 22, 2017 (JP) .................................. 2017-247012

(51) Int. Cl.
*A61B 1/00* (2006.01)
*A61B 1/04* (2006.01)
(Continued)

(52) U.S. Cl.
CPC ...... *A61B 1/00009* (2013.01); *A61B 1/00006* (2013.01); *A61B 1/00045* (2013.01);
(Continued)

(58) Field of Classification Search
CPC ............ A61B 1/00009; A61B 1/00006; A61B 1/00045; A61B 1/043; A61B 1/045;
(Continued)

(56) References Cited

U.S. PATENT DOCUMENTS 7,062,311 B1 6/2006 Sendai et al.
2002/0013512 A1 1/2002 Sendai et al.
(Continued)

FOREIGN PATENT DOCUMENTS

EP 1 067 376 A2 1/2001
JP 2001-078175 A 3/2001
(Continued)

OTHER PUBLICATIONS

International Search Report dated Jan. 15, 2019 together with an English language translation.

*Primary Examiner* — Timothy J Neal
*Assistant Examiner* — James Edward Boice
(74) *Attorney, Agent, or Firm* — Scully, Scott, Murphy & Presser, P.C.

(57) ABSTRACT

An endoscope system includes a processor configured to generate a clock at predetermined timing, a light source apparatus configured to irradiate white light and excitation light in a time division manner in synchronization with the clock, and an endoscope configured to perform image pickup based on irradiation timing of the light source apparatus. The processor generates a first white light image at a first clock, generates a first fluorescent image at a second clock, generates a second white light image at a third clock, and generates a third white light image at a fourth clock and superimposes the second white light image and the first fluorescent image at the fourth clock and superimposes the third white light image and the first fluorescent image at a fifth clock.

13 Claims, 6 Drawing Sheets

(51) Int. Cl.
*A61B 1/045* (2006.01)
*A61B 1/05* (2006.01)
*A61B 1/06* (2006.01)

(52) U.S. Cl.
CPC .............. *A61B 1/043* (2013.01); *A61B 1/045* (2013.01); *A61B 1/05* (2013.01); *A61B 1/0661* (2013.01)

(58) Field of Classification Search
CPC ........... A61B 1/05; A61B 1/0661; A61B 1/00; A61B 1/06; A61B 1/000095; A61B 1/0005; A61B 3/0058; A61B 2576/00; A61B 1/063; A61B 1/0638; G02B 23/24; G02B 23/26; H04N 7/18
USPC ....................................................... 600/160
See application file for complete search history.

(56) References Cited

U.S. PATENT DOCUMENTS

2002/0161282 A1* 10/2002 Fulghum .................. A61B 1/07
600/178
2010/0094136 A1* 4/2010 Nakaoka .................. A61B 1/05
600/178

FOREIGN PATENT DOCUMENTS

| JP | 2001-327458 A | 11/2001 |
| JP | 2012-157559 A | 8/2012 |
| JP | 6205531 B1 | 9/2017 |
| WO | 2018/047369 A1 | 3/2018 |

* cited by examiner

ENDOSCOPE SYSTEM AND CONTROL METHOD FOR ENDOSCOPE SYSTEM

CROSS REFERENCE TO RELATED APPLICATION

This application is a continuation application of PCT/JP2018/038315 filed on Oct. 15, 2018 and claims benefit of Japanese Application No. 2017-247012 filed in Japan on Dec. 22, 2017, the entire contents of which are incorporated herein by this reference.

BACKGROUND OF THE INVENTION

1. Field of the Invention

Embodiments of the present invention relate to an endoscope system and a control method for the endoscope system and, more particularly, to an endoscope system used for fluorescence observation and a control method for the endoscope system.

2. Description of the Related Art

In a medical field, fluorescence observation for administering a fluorescent marker such as ICG to a subject and thereafter irradiating excitation light and picking up an image of marker fluorescent light emitted from the administered marker to specify a blood vessel or a lymph vessel and confirm a blood flow has been widely performed conventionally.

Since a signal obtained by the marker fluorescent light is feeble, a fluorescent image is an unclear image. Therefore, in order to obtain a clear image, an endoscope system that acquires a fluorescent image and a white light image in a time division manner and displays a superimposed combined image has been proposed (see, for example, Japanese Patent Application Laid-Open Publication No. 2012-157559).

SUMMARY OF THE INVENTION

An endoscope system according to an aspect of the present invention includes: a processor configured to generate a clock at predetermined timing; a light source apparatus configured to irradiate white light and excitation light in a time division manner in synchronization with the clock; and an endoscope configured to perform image pickup based on irradiation timing of the light source apparatus, in which when generating a white light image based on a signal obtained by the endoscope at timing for irradiating the white light, based on the generated clock, the processor generates a first white light image at a first clock, generates a second white light image at a third clock, and generates a third white light image at a fourth clock, when generating a fluorescent image based on a signal obtained by the endoscope at timing for irradiating the excitation light, the processor generates, based on the generated clock, a first fluorescent image at a second clock, and when superimposing the generated white light image and the generated fluorescent image to generate a superimposed image, based on the generated clock, the processor superimposes the second white light image and the first fluorescent image at the fourth clock and superimposes the third white light image and the first fluorescent image at a fifth clock.

A control method for an endoscope system according to an aspect of the present invention includes: generating a clock at predetermined timing; irradiating white light and excitation light in a time division manner in synchronization with the clock; performing image pickup based on irradiation timing; when generating a white light image based on a signal obtained at timing for irradiating the white light, based on the generated clock, generating a first white light image at a first clock, generating a second white light image at a third clock, and generating a third white light image at a fourth clock; when generating a fluorescent image based on a signal obtained at timing for irradiating the excitation light, generating, based on the generated clock, a first fluorescent image at a second clock; and, when superimposing the generated white light image and the generated fluorescent image to generate a superimposed image, based on the generated clock, superimposing the second white light image and the first fluorescent image at the fourth clock and superimposing the third white light image and the first fluorescent image at a fifth clock.

DETAILED DESCRIPTION OF THE PREFERRED EMBODIMENTS

Embodiments are explained below with reference to the drawings.

First Embodiment

Figure 1:
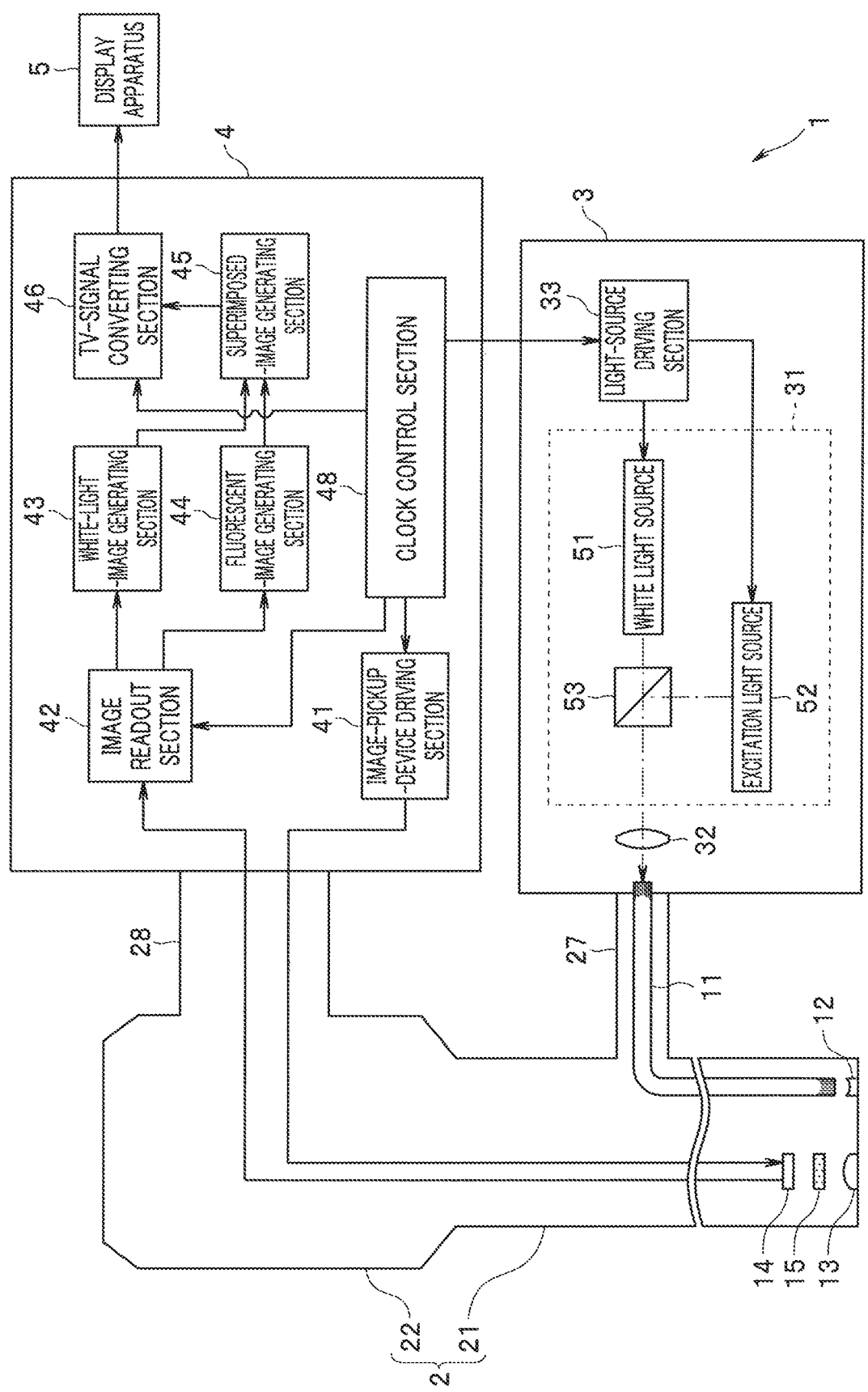
FIG. 1 is a block diagram for explaining an example of an overall configuration of an endoscope system according to a first embodiment of the present invention.

FIG. 1 is a block diagram for explaining an example of an overall configuration of an endoscope system according to a first embodiment of the present invention.

An endoscope system 1 includes, for example, as shown in FIG. 1, an endoscope 2 inserted into a body cavity of a subject and configured to pick up an image of an object such as a biological tissue present in the body cavity and output an image pickup signal, a light source apparatus 3 configured to supply light irradiated on the object to the endoscope 2, a processor 4 configured to apply various processing to the image pickup signal outputted from the endoscope 2 to thereby generate an observation image and output the observation image, and a display apparatus 5 configured to display, on a screen, the observation image outputted from the processor 4.

The endoscope 2 includes, for example, as shown in FIG. 1, an insertion section 21 formed in an elongated shape insertable into the body cavity of the subject and an operation section 22 provided on a proximal end side of the insertion section 21. The endoscope 2 includes a configuration detachably attachable to the light source apparatus 3 via a light guide cable 27. The endoscope 2 includes a configuration detachably attachable to the processor 4 via a signal cable 28 extended from the operation section 22.

A light guide 11 for transmitting the light supplied from the light source apparatus 3 is inserted through insides of the insertion section 21 and the light guide cable 27.

As shown in FIG. 1, an emission end portion of the light guide 11 is disposed near an illumination lens 12 at a distal end portion of the insertion section 21. As shown in FIG. 1, an incident end portion of the light guide 11 is disposed near a condensing lens 32 in the light source apparatus 3 connected to the endoscope 2 via the light guide cable 27.

The illumination lens 12 for emitting the light transmitted by the light guide 11 to an outside and an objective lens 13 for receiving light made incident from the outside are provided at the distal end portion of the insertion section 21. An image pickup device 14 and an excitation light cut filter 15 disposed on an optical path extending from the objective lens 13 to the image pickup device 14 are provided at the distal end portion of the insertion section 21.

The image pickup device 14 includes, for example, a color CMOS image sensor, to an image pickup surface of which a color filter of a primary color system or a complementary color system is attached. The image pickup device 14 is configured to perform an image pickup operation corresponding to an image pickup device driving signal outputted from the processor 4. The image pickup device 14 is configured to pick up an image of light transmitted through the excitation light cut filter 15 and generate an image pickup signal and output the generated image pickup signal to the processor 4.

The excitation light cut filter 15 is formed to have, for example, an optical characteristic of cutting off the same wavelength band as a wavelength band of excitation light EXA (explained below) and transmitting a wavelength band different from the wavelength band of the excitation light EXA among respective wavelength bands included in light emitted through the objective lens 13. In other words, the excitation light cut filter 15 is formed to have an optical characteristic of transmitting fluorescent light FLA (explained below) emitted from a fluorescent marker according to irradiation of the excitation light EXA.

In other words, an image pickup section in the embodiment includes the image pickup device 14 and the excitation light cut filter 15.

The operation section 22 is provided on the proximal end side of the insertion section 21 and formed to have a shape that can be gripped by a user such as a surgeon. In the operation section 22, for example, a scope switch (not shown), which is one or more switches capable of giving various instructions corresponding to operation by the user to the processor 4, is provided.

The light source apparatus 3 functioning as an illuminating section includes, for example, as shown in FIG. 1, a light emitting section 31, a condensing lens 32, and a light-source driving section 33.

The light emitting section 31 includes a white light source 51, an excitation light source 52, and a dichroic mirror 53.

The white light source 51 includes, for example, any one of a xenon lamp, a white LED, and LEDs of three colors of red, green, and blue. The white light source 51 is configured to generate, according to a light source driving signal outputted from the light-source driving section 33, for example, white light WLA, which is light including respective wavelength bands of a red region, a green region, and a blue region. Note that in the embodiment, instead of the white light source 51, for example, a wide-band light source including a lamp that emits wide-band light, which is light having a wavelength band of at least a blue region to a near infrared region, and an optical filter having an optical characteristic of transmitting the same wavelength band as a wavelength band of the white light WLA and cutting off the other wavelength bands among respective wavelength bands included in the wide-band light may be provided in the light source apparatus 3.

The excitation light source 52 includes, for example, an LD (laser diode). The excitation light source 52 is configured to generate, according to the light source driving signal outputted from the light-source driving section 33, for example, the excitation light EXA, which is narrow-band light including an excitation wavelength of a predetermined fluorescent marker administered to the subject. Note that in the following explanation, unless particularly referred to otherwise, it is assumed that the fluorescent marker administered to the subject is ICG (indocyanine green), the excitation light EXA is narrow-band near infrared light including an excitation wavelength of the ICG, and the fluorescent light FLA, which is near infrared light belonging to a wavelength band on a longer wavelength side than the excitation light EXA, is emitted from the ICG.

The dichroic mirror 53 has, for example, an optical characteristic of transmitting the white light WLA emitted from the white light source 51 and emitting the white light WLA to the condensing lens 32 side and reflecting the excitation light EXA emitted from the excitation light source 52 and emitting the excitation light EXA to the condensing lens 32 side.

In other words, the light emitting section 31 is configured to be able to generate the white light WLA by causing the white light source 51 to emit light according to a driving signal outputted from the light-source driving section 33. The light emitting section 31 is configured to be able to generate the excitation light EXA by causing the excitation light source 52 to emit light according to the driving signal outputted from the light-source driving section 33. The light emitting section 31 is configured to be able to emit the white light WLA and the excitation light EXA to the condensing lens 32.

The condensing lens 32 is configured to condense light emitted from the light emitting section 31 and emitting the light to the incident end portion of the light guide 11.

The light-source driving section 33 is configured to generate, based on a control signal outputted from the processor 4, a light source driving signal for driving the white light source 51 and the excitation light source 52 and output the light source driving signal to the light emitting section 31.

In other words, the light source apparatus 3 is configured to be able to emit the excitation light EXA for exciting the fluorescent marker administered to the subject and the white light WLA, which is illumination light for illuminating an inside of the body cavity of the subject.

The processor 4 includes, for example, as shown in FIG. 1, an image-pickup-device driving section 41, an image readout section 42, a white-light-image generating section 43, a fluorescent-image generating section 44, a superimposed-image generating section 45, a TV-signal converting section 46, and a clock control section 48. Note that according to the embodiment, for example, the respective sections of the processor 4 may be configured as respective electronic circuits or may be configured as circuit blocks in an integrated circuit such as an FPGA (field programmable gate array).

The image-pickup-device driving section 41 is configured to generate, based on a control signal outputted from the clock control section 48, an image pickup device driving signal for driving the image pickup device 14 and output the image pickup device driving signal.

The image readout section 42 is configured to perform, based on the control signal outputted from the clock control section 48, operation for setting an output destination of an image pickup signal, which is outputted from the endoscope 2, to either the white-light-image generating section 43 or the fluorescent-image generating section 44.

The white-light-image generating section 43 is configured to generate a white light image WIA based on an image pickup signal outputted through the image readout section 42 and output the generated white light image WIA to the superimposed-image generating section 45. In other words, the white-light-image generating section 43 is configured to generate the white light image WIA, which is an image corresponding to reflected light of the white light WLA, an image of which is picked up by the image pickup device 14.

The fluorescent-image generating section 44 is configured to generate the fluorescent image FIA based on the image pickup signal outputted through the image readout section 42 and output the generated fluorescent image FIA to the superimposed-image generating section 45. In other words, the fluorescent-image generating section 44 is configured to generate the fluorescent image FIA, which is an image corresponding to the fluorescent light FLA, an image of which is picked up by the image pickup device 14.

The superimposed-image generating section 45 functioning as an image superimposing section is configured to be able to perform operation corresponding to the control signal outputted from the clock control section 48. The superimposed-image generating section 45 is configured to generate a superimposed image SIA by performing processing for superimposing the white light image WIA outputted from the white-light-image generating section 43 and the fluorescent image FIA outputted from the fluorescent-image generating section 44 and output the generated superimposed image SIA to the TV-signal converting section 46.

The TV-signal converting section 46 functioning as a signal converting section converts, based on the control signal outputted from the clock control section 48, the superimposed image SIA inputted from the superimposed-image generating section 45 into a video signal of a type displayable on the display apparatus 5.

The clock control section 48 functioning as a clock generating section and a clock control section is configured to generate control signals for synchronizing generation timings for the white light WLA and the excitation light EXA in the light emitting section 31, an image pickup operation in the image pickup device 14, and an output destination of an image pickup signal inputted to the processor 4 and output the control signals respectively to the light-source driving section 33, the image-pickup-device driving section 41, and the image readout section 42. The clock control section 48 outputs, to the TV-signal converting section 46, a control signal for controlling an output operation for a video signal outputted to the display apparatus 5. Note that timings of all the control signals are adjusted based on generation timings for frames or fields of the video signal outputted to the display apparatus 5.

Next, operation and the like of the endoscope system 1 in the embodiment are explained. Note that in the following explanation, it is assumed that, before fluorescent observation of a desired object present in a body cavity of a subject is performed, ICG (a fluorescent marker) is administered to the desired object in advance. In the following explanation, for simplification, explanation concerning white light observation, which is an observation method for causing the display apparatus 5 to display, as an observation image, the white light image WIA obtained by picking up an image of the object on which the white light WLA is irradiated, is omitted.

First, after connecting the respective sections of the endoscope system 1 and turning on a power supply, for example, the user operates a fluorescent observation start switch (not shown) to thereby give an instruction for starting the fluorescent observation of the object to the clock control section 48. The user inserts the insertion section 21 into the body cavity of the subject to thereby dispose the distal end portion of the insertion section 21 near the desired object present in the body cavity.

When a power supply of the processor 4 is turned on, the clock control section 48 generates a control signal for controlling output timings for a video signal and outputs the control signal to the TV-signal converting section 46. When detecting the instruction from the fluorescent observation start switch, the clock control section 48 generates, based on timings of the control signal for controlling the output timings for the video signal, control signals for synchronizing generation timings for the white light WLA and the excitation light EXA in the light emitting section 31, an image pickup operation in the image pickup device 14, and an output destination of an image pickup signal inputted to the processor 4 and outputs the control signals respectively to the light-source driving section 33, the image-pickup-device driving section 41, and the image readout section 42.

Figure 2:
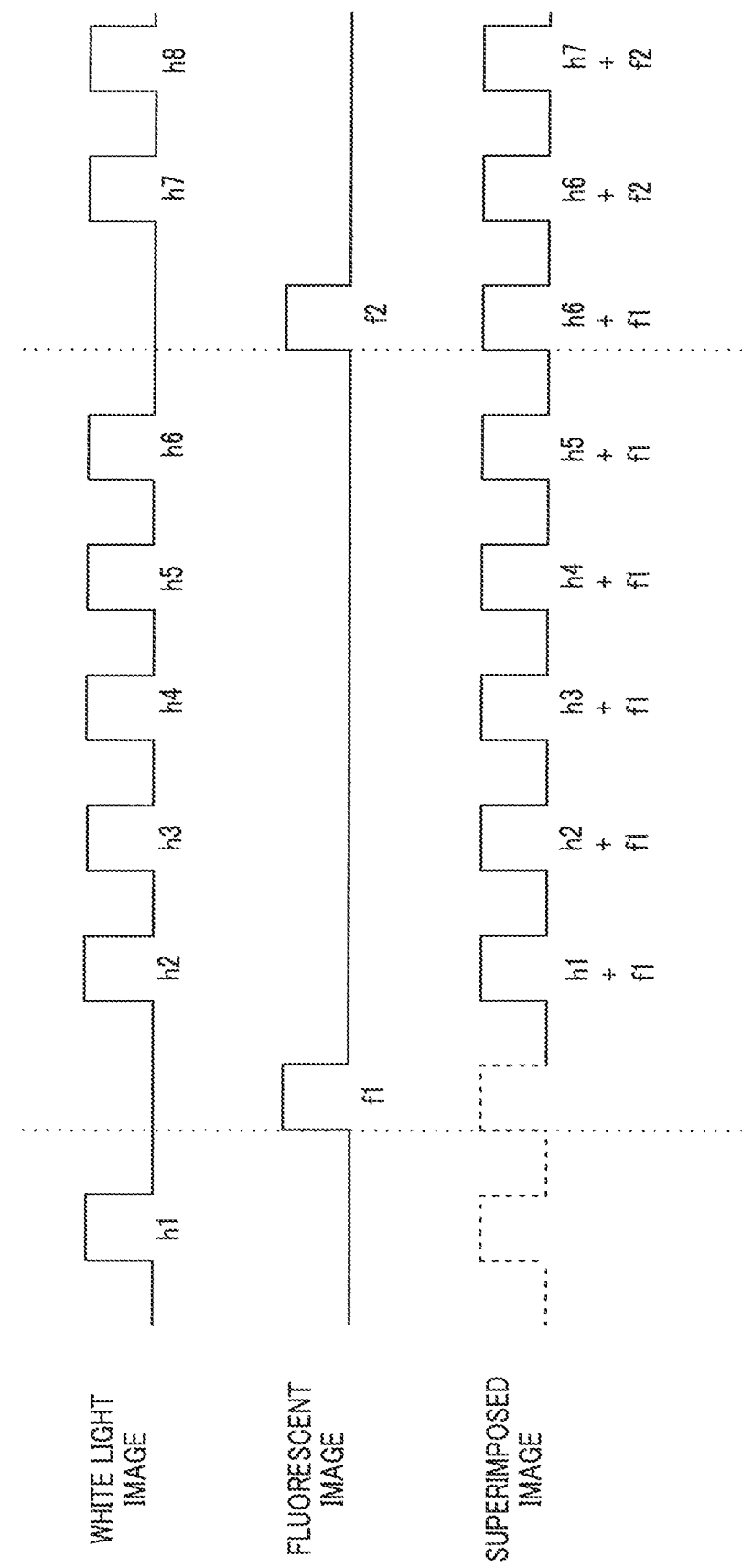
FIG. 2 is a timing chart for explaining an example of image pickup timings for a white light image and a fluorescent image according to the first embodiment.

FIG. 2 is a timing chart for explaining an example of image pickup timings for a white light image and a fluorescent image according to the first embodiment. As shown in FIG. 2, in the embodiment, all of image pickup timings for the white light image WIA, image pickup timings for the fluorescent image FIA, and generation timings for the superimposed image SIA, which is a video signal, are generated at the same clocks.

Approximately 80% to 90% of the generation timings for the superimposed image SIA is used for generation of the white light image WIA and approximately 10% to 20% of the generation timings is used for generation of the fluorescent image FIA. In other words, at the generation timings for the superimposed image SIA, after the white light image WIA is continuously generated approximately five times to nine times, the fluorescent image FIA is generated once. For example, as shown in FIG. 2, it is conceived that, a period of continuously generating five images of the white light image WIA and thereafter generating the fluorescent image FIA once is repeated to generate the superimposed image SIA. In this case, a frame rate of the fluorescent image FIA is one sixth of a frame rate of the superimposed image SIA. However, one frame of the white light image WIA is lost every time seven frames of the superimposed image SIA are generated. However, continuously picked-up images for six frames of the white light image WIA can be acquired at the same rate as the superimposed image SIA. Accordingly, compared with when the white light image WIA and the fluorescent image FIA are alternately generated (in a time division manner), a frame rate of the white light image WIA increases. Therefore, it is possible to generate a video having a more natural and smoother movement.

Note that the superimposed image SIA is generated by superimposing the white light image WIA and the fluorescent image FIA picked up immediately before the generation of the superimposed image SIA. For example, when a white light image h1 is generated at a first clock, a fluorescent image f1 is generated at a second clock, white light images h2 to h6 are generated at third to seventh clocks, a fluorescent image f2 is generated at an eighth clock, and white light images h7 and h8 are generated at ninth and tenth clocks, the superimposed image FIA is generated as explained below. In other words, the white light image h1 generated at the first clock and the fluorescent image f1 generated at the second clock are superimposed at the third clock. The white light image h2 generated at the third clock and the fluorescent image generated at the second clock are superimposed at the fourth clock. The white light image h3 generated at the fourth clock and the fluorescent image f1 generated at the second clock are superimposed at the fifth clock.

Specifically, the clock control section 48 generates, for example, a control signal for causing the image pickup device 14 to perform an image pickup operation of a rolling shutter type and outputs the control signal to the image-pickup-device driving section 41. For example, in each blanking period, which is a period in which readout is not performed in all lines of the image pickup device 14 in the image pickup operation of the rolling shutter type, the clock control section 48 generates a control signal for generating the white light WLA having a light amount AL1 and the excitation light EXA having the light amount AL1 at the timings described above and outputs the control signal to the light-source driving section 33. In other words, the clock control section 48 generates a control signal and outputs the control signal to the light-source driving section 33 to generate the excitation light EXA once every time the white light WLA is continuously generated the number of times (for example, five times) set in advance.

The clock control section 48 generates, for example, a control signal for setting, to the white-light-image generating section 43, an output destination of an image pickup signal inputted to the processor 4 when the white light WLA is generated and setting, to the fluorescent-image generating section 44, an output destination of an image pickup signal inputted to the processor 4 when the excitation light EXA is generated and outputs the control signal to the image readout section 42.

According to the control by the clock control section 48 explained above, for example, the white light WLA is irradiated on an object in a first blanking period, third to seventh blanking periods, and ninth and tenth blanking periods of the image pickup device 14, an image of reflected light of the white light WLA, which is return light generated from the object, is picked up by the image pickup device 14, an image pickup signal generated by the image pickup device 14 is outputted to the white-light-image generating section 43 through the image readout section 42, and the white light image WIA generated based on the image pickup signal is outputted to each of the superimposed-image generating section 45 and the TV-signal converting section 46.

According to the control by the clock control section 48 explained above, for example, the excitation light EXA is irradiated on the object in the second, eighth blanking periods of the image pickup device 14 different from the first, third to seventh blanking periods, that is, at timing of once in six times of blanking periods, an image of the florescent light FLA included in return light generated from the object is picked up by the image pickup device 14, an image pickup signal generated by the image pickup device 14 is outputted to the fluorescent-image generating section 44 through the image readout section 42, and the fluorescent image FIA generated based on the image pickup signal is outputted to the superimposed-image generating section 45.

The superimposed-image generating section 45 generates the superimposed image SIA by performing processing for superimposing the white light image WIA outputted from the white-light-image generating section 43 and the fluorescent image FIA outputted from the fluorescent-image generating section 44 and outputs the generated superimposed image SIA to the TV-signal converting section 46. In other words, according to such operation of the superimposed-image generating section 45, the superimpose image SIA, in which a generation part of the florescent light FLA in the object, an image of which is picked up by the endoscope 2, is indicated by green, is outputted to the TV-signal converting section 46.

The TV-signal converting section 46 outputs, based on a control signal outputted from the clock control section 48, the superimposed image SIA outputted from the superimposed-image generating section 45 to the display apparatus 5 as an observation image.

As explained above, with the endoscope system 1 in the embodiment, the fluorescent image FIA is acquired once in each number of frames (for example, six frames) set in advance and the white light image WIA is acquired in continuous frames (for example, continuous five frames) during acquisition of the fluorescent image FIA. Therefore, it is possible to continuously update, as much as possible, information indicating structure such as unevenness of a biological tissue included in the white light image WIA and cause the display apparatus 5 to display an observation image to which information indicating a generation part of the florescent light FLA included in the superimposed image SIA is given. Therefore, according to the embodiment, when fluorescent light emitted from the biological tissue is observed, it is possible to realize a video having a smooth and natural movement.

Note that according to the embodiment, the configuration of the endoscope system 1 may be modified as appropriate to be adapted to other fluorescent markers other than the ICG.

Specifically, for example, when the fluorescent marker administered to the subject is fluorescein, what should be done is only to emit blue light in a narrow band including an excitation wavelength of the fluorescein from the excitation light source 52 as excitation light EXB, provide, instead of the dichroic mirror 53, a half mirror that transmits the white light WLA and reflects the excitation light EXB, cut off light in the same wavelength band as the wavelength band of the excitation light EXB in the excitation light cut filter 15, and transmit light in a visible region including fluorescent light FLB, which is green light emitted from the fluorescein according to irradiation of the excitation light EXB, through the excitation light cut filter 15.

Timing for acquiring the fluorescent image FIA is not fixed to preset timing (for example, one frame in every continuous six frames). For example, the user may be able to freely set the timing from the outside or may dynamically adjust the timing according to luminance of the florescent image FIA.

Figure 3:
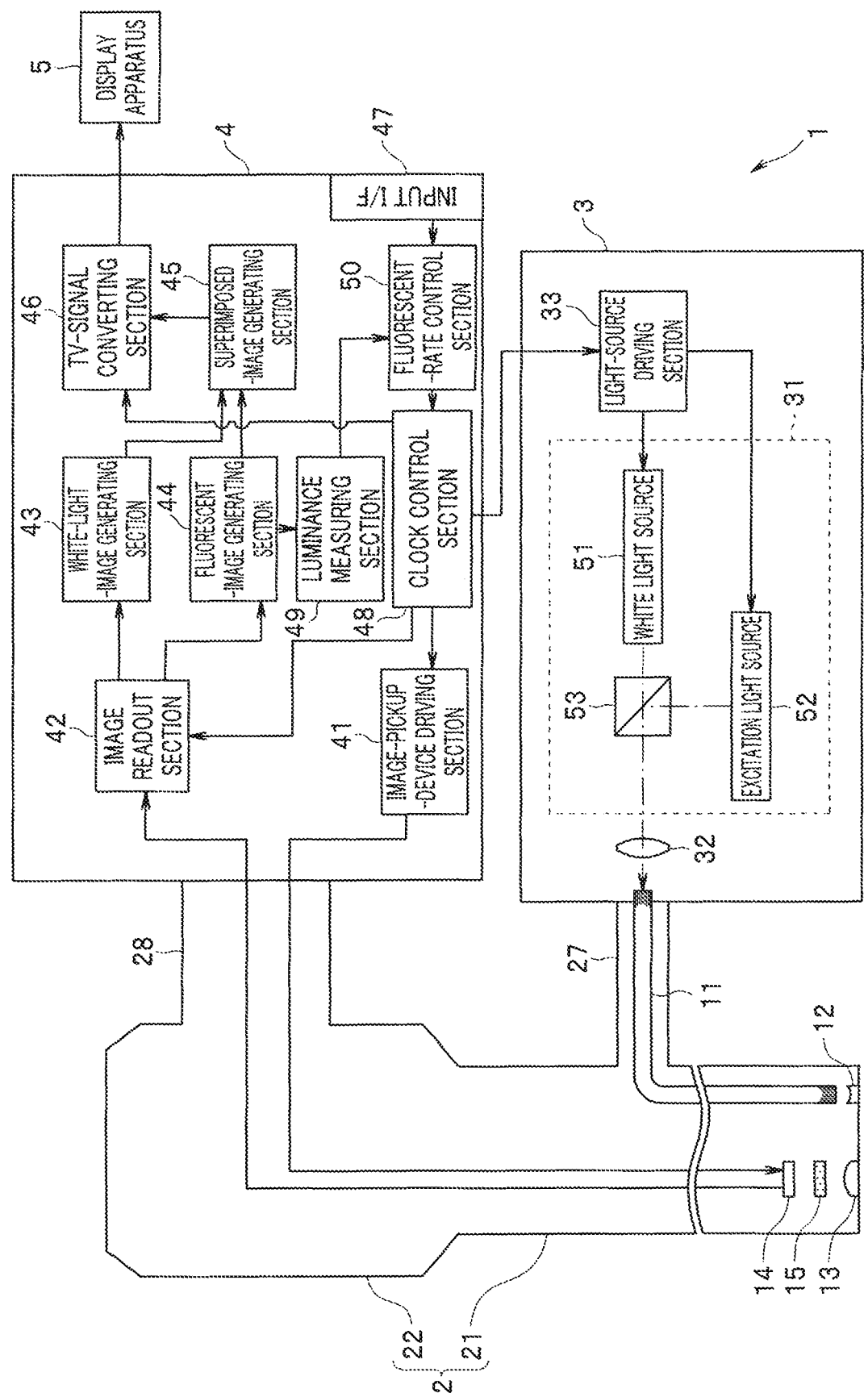
FIG. 3 is a block diagram for explaining another example of the overall configuration of the endoscope system according to the first embodiment of the present invention.

FIG. 3 is a block diagram for explaining another example of the overall configuration of the endoscope system according to the embodiment of the present invention. For example, as shown in FIG. 3, in addition to the components shown in FIG. 1, an input I/F 47 that enables the user to set acquisition timing of a fluorescent image, a luminance measuring section 49 that measures luminance of the fluorescent image FIA generated by the fluorescent-image generating section 44, and a fluorescent-rate control section 50 that sets timing for acquiring the fluorescent image FIA are further provided in the processor 4.

In the input I/F 47, when the user sets timing for fluorescent light acquisition, the set timing is outputted to the fluorescent-rate control section 50. The fluorescent-rate control section 50 acquires the fluorescent image FIA at the inputted timing and outputs a control signal to the clock control section 48 to continuously acquire the white light image WIA in frames during the acquisition of the fluorescent image FIA.

When the timing for the fluorescent light acquisition is dynamically changed according to the luminance of the fluorescent image FIA, the luminance of the fluorescent image FIA generated by the fluorescent-image generating section 44 is measured by the luminance measuring section 49 and a measurement result is outputted to the fluorescent-rate control section 50. When the inputted luminance is lower than preset reference luminance, the fluorescent-rate control section 50 outputs a control signal to the clock control section 48 to increase an acquisition rate of the fluorescent image FIA.

The clock control section 48 outputs control signals to the image-pickup-device driving section 41, the image readout section 42, the light-source driving section 33, and the TV-signal readout section 48 according to the inputted timing.

By dynamically changing the acquisition rate of the florescent image FIA in this way, it is possible to secure a smooth and natural movement and realize a video in which an occurrence part of the fluorescent light FLA is more easily observed.

Second Embodiment

In the first embodiment explained above, the generation clock for the image pickup signal for acquiring the white light image WIA and the fluorescent image FIA is acquired at the same clock as the output clock for the video signal displayed on the display apparatus 5. On the other hand, a second embodiment is different in that an acquisition rate of the white light image WIA and the fluorescent image FIA (a clock of the image pickup device 14) is generated using a clock at timing earlier than timing for generating the video signal displayed on the display apparatus 5.

A configuration of the endoscope system 1 in the embodiment is the same as the configuration of the endoscope system in the first embodiment explained with reference to FIG. 1. Therefore, the same components are denoted by the same reference numerals and signs and explanation of the components is omitted. Operating parts different from the operating parts of the endoscope system 1 in the first embodiment are explained below.

Figure 4:
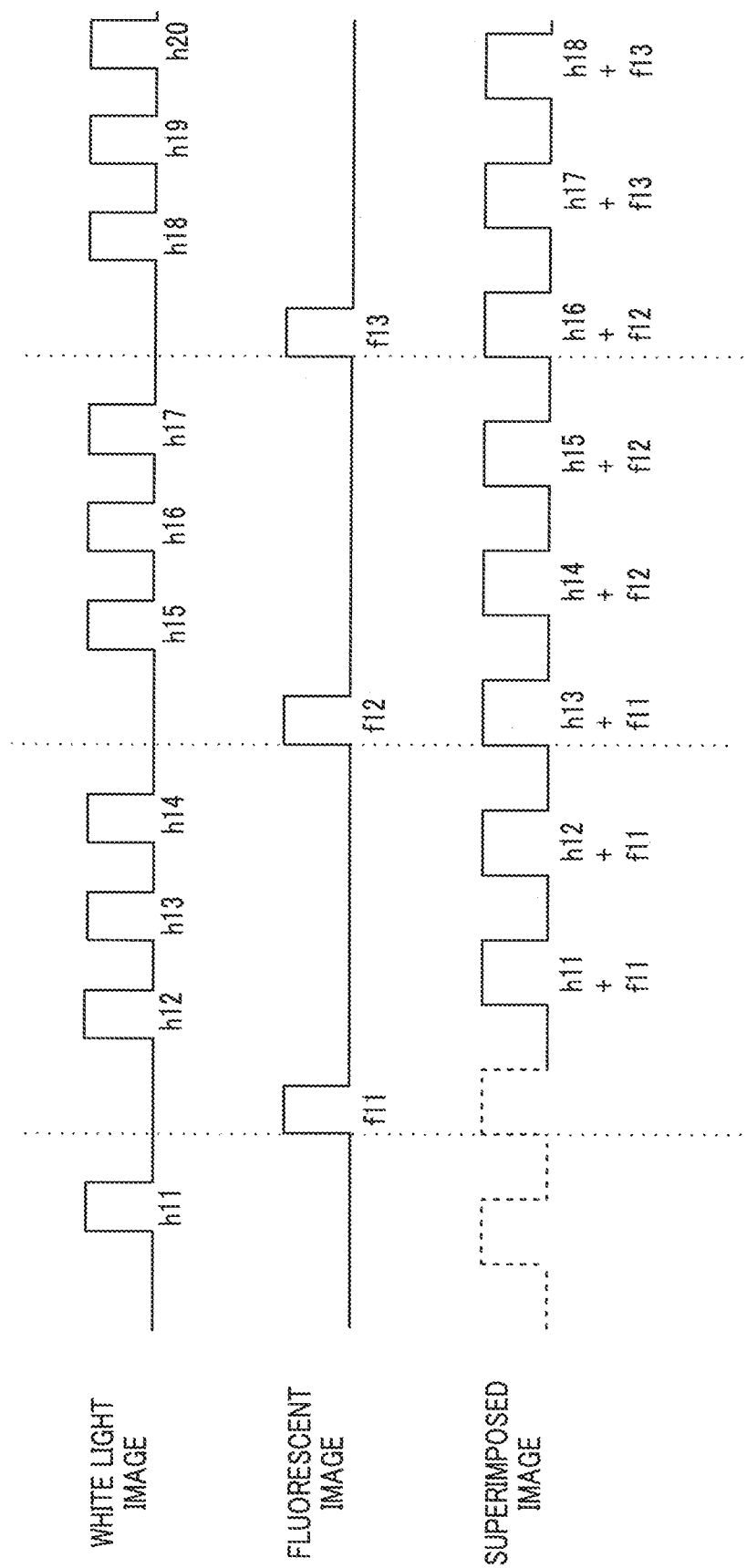
FIG. 4 is a timing chart for explaining an example of image pickup timings for a white light image and a fluorescent image according to a second embodiment.

FIG. 4 is a timing chart for explaining an example of image pickup timings for a white light image and a fluorescent image according to the second embodiment. As shown in FIG. 4, in the embodiment, image pickup timings for the white light image WIA and image pickup timings for the fluorescent image FIA are the same clocks but are generated at clocks different from generation timings for the superimposed image SIA, which is a video signal. The image pickup timings are generated at clocks earlier than the generation timings for the superimposed image SIA. For example, in the example shown in FIG. 4, as generation clocks for an image pickup signal, clocks of approximately 1.3 times of generation clocks for the superimposed image SIA, that is, output clocks of the video signal are used.

This is timing for picking up an image for four frames while the video signal for three frames is outputted. Among the four times of the image pickup timings, three times are allocated to image pickup of the white light image WIA and image pickup of the fluorescent image FIA is performed in the remaining one time. In other words, the white light image WIA for three frames can be acquired while the superimposed image SIA for three frames is generated. Therefore, since a frame rate of the white light image WIA does not decrease, it is possible to generate a video having a natural and smooth movement.

Note that as in the first embodiment explained with reference to FIG. 2, the superimposed image SIA is generated by superimposing the white light image WIA and the fluorescent image FIA picked up immediately before the generation of the superimposed image SIA.

In this way, with the endoscope system 1 in the embodiment, generation clocks for the image pickup signal are set to n times (n is a decimal or an integer larger than 1) of output clocks for the video signal. Clocks are allocated to the white light image WIA such that the number of clocks in a unit time period is the same as the number of clocks of the video signal. The remaining clocks are allocated to the fluorescent image FIA. Therefore, it is possible to acquire the florescent image FIA and set a frame rate of the white light image WIA to the same rate as a frame rate of the video signal. Therefore, it is possible to secure continuity of the white light image WIA. When fluorescent light emitted from a biological tissue is observed, it is possible to realize a video having a smooth and natural movement.

Note that in the embodiment as well, the endoscope system 1 having the configuration shown in FIG. 3 may be used. A user may be able to manually set, with the input 1F 47, a rate of generation clocks for the image pickup signal, that is, to how many times of output clocks of the video signal the rate is set. The rate may be able to be automatically changed according to luminance in the fluorescent image FIA. In this case, when inputted luminance is lower than preset reference luminance, the fluorescent-rate control section 50 outputs a control signal to the clock control section 48 to increase the rate of the generation clocks for the image pickup signal. By increasing the generation rate of the image pickup signal, it is possible to increase a generation rate of the fluorescent image FIA without reducing a generation rate of the white light image WIA. Therefore, in the superimposed image SIA, it is possible to more clearly display a generation part of the florescent light FLA.

Third Embodiment

In the first and second embodiments explained above, when the white light image WIA and the fluorescent image FIA are acquired, the image pickup signal is read out from the image pickup device 14 pixel by pixel and outputted. On the other hand, a third embodiment is different in that, when an image pickup signal is outputted from the image pickup device 14 for both of the white light image WIA and the fluorescent image FIA, a plurality of pixel information are collectively outputted by binning.

A configuration of the endoscope system 1 in the embodiment is the same as the configuration of the endoscope system in the first embodiment explained with reference to FIG. 1. Therefore, the same components are denoted by the same reference numerals and signs and explanation of the components is omitted. Operating parts different from the operating parts of the endoscope system 1 in the first embodiment are explained below.

Figure 5:
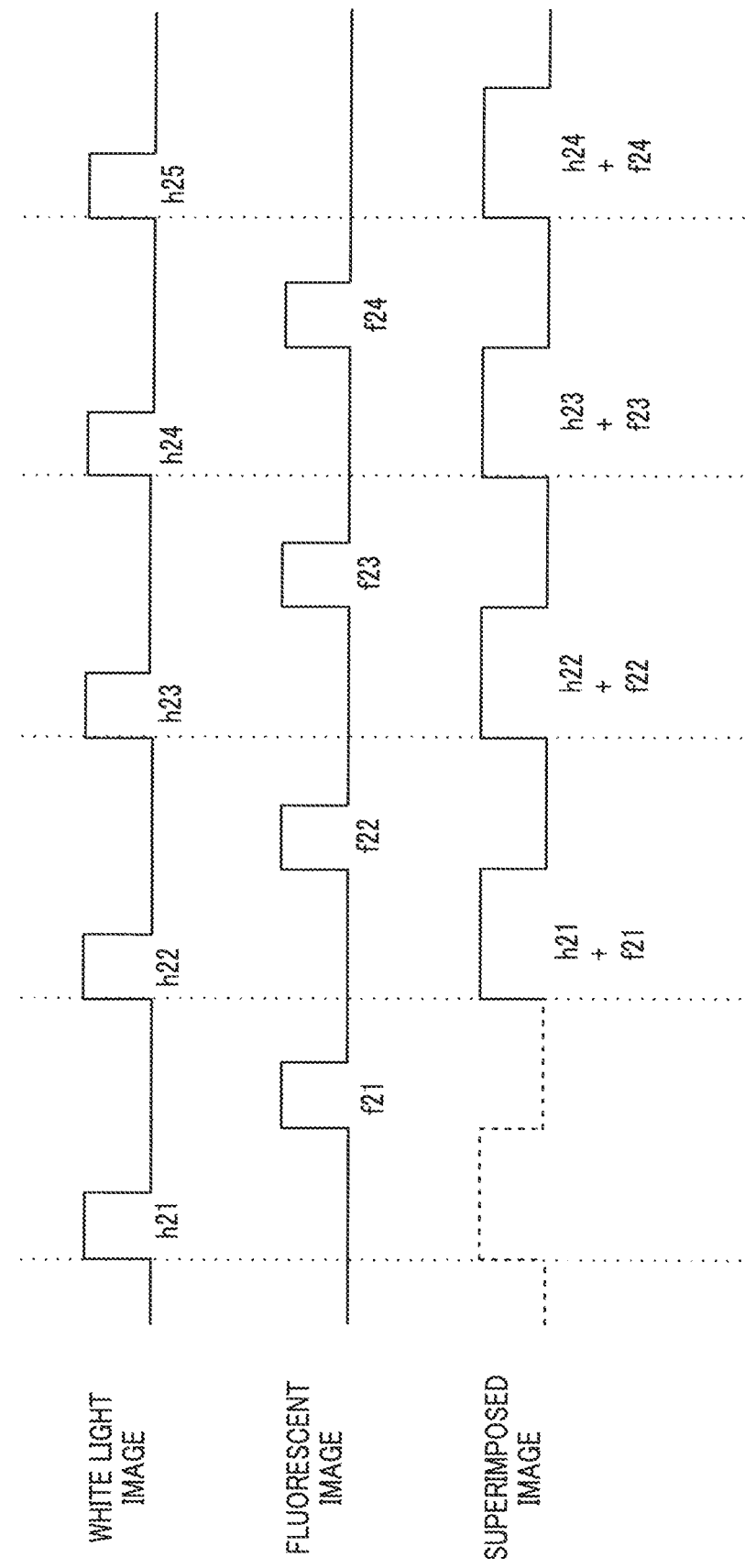
FIG. 5 is a timing chart for explaining an example of image pickup timings for a white light image and a fluorescent image according to a third embodiment.

FIG. 5 is a timing chart for explaining an example of image pickup timings for a white light image and a fluorescent image according to the third embodiment. FIG. 5 shows a case in which pixel information for two pixels is collectively outputted from the image pickup device 14. By collectively outputting the information for the two pixels, an output time period for an image pickup signal for one frame is halved. In other words, a frame rate can be doubled compared with when pixel information is read out pixel by pixel.

Therefore, even when the white light image WIA and the fluorescent image FIA are switched and generated in a time division manner, a frame rate of the superimposed image SIA and a frame rate of the white light image WIA can be equalized. Therefore, it is possible to generate a video having a natural and smooth movement.

Note that the number of pixels collectively outputted by the binning is not limited to two. By collectively outputting more pixels such as 2×2=4 pixels, it is also possible to further increase the frame rates of the white light image WIA and the fluorescent image FIA.

Fourth Embodiment

In the first to third embodiments explained above, the clock control section 48 generates, based on timing of a control signal for controlling an output timing of a video signal, control signals for synchronizing generation timings for the white light WLA and the excitation light EXA in the light emitting section 31, an image pickup operation in the image pickup device 14, and an output destination of an image pickup signal inputted to the processor 4 and outputs the control signals respectively to the light-source driving section 33, the image-pickup-device driving section 41, and the image readout section 42. On the other hand, a fourth embodiment is different in that a control signal for controlling output timing for a video signal and control signals for controlling generation timings for the white light image WIA and the fluorescent image FIA are independently generated.

Figure 6:
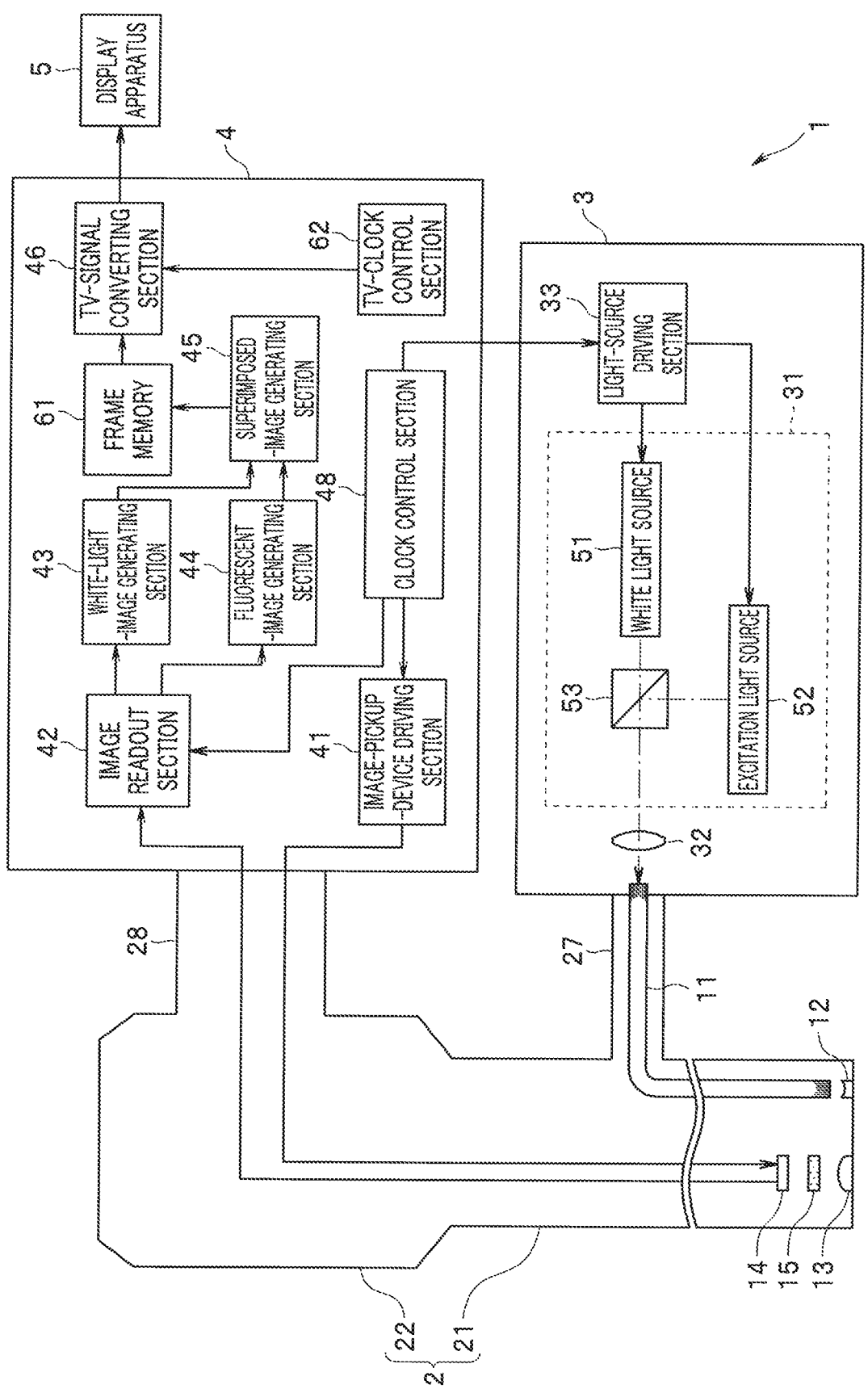
FIG. 6 is a block diagram for explaining an example of an overall configuration of an endoscope system according to a fourth embodiment of the present invention.

FIG. 6 is a block diagram for explaining an example of an overall configuration of an endoscope system according to the fourth embodiment of the present invention. A configuration of the endoscope system 1 shown in FIG. 6 is the same as the configuration of the endoscope system in the first embodiment explained with reference to FIG. 1 except that a frame memory 61 and a TV-clock control section 62 are provided in the processor 4. Therefore, the same components are denoted by the same reference numerals and signs and explanation of the components is omitted.

The frame memory 61 stores the superimposed image SIA outputted from the superimposed-image generating section 45. The TV-clock control section 62 generates output timing for a video signal according to input specifications of the video signal displayable on the display apparatus 5 and outputs the output timing to the TV-signal converting section 46 as a control signal.

The TV-signal converting section 46 acquires the superimposed image SIA from the frame memory 61 at predetermined timing according to the control signal inputted from the TV-clock control section 62 and outputs the superimposed image SIA to the display apparatus 5.

By adopting such a configuration, it is unnecessary to adjust generation timings for the white light image WIA and the fluorescent image FIA according to the output timing for the video signal. In other words, even when the display apparatus 5 having input specifications of the video signal different from input specifications of a display apparatus used before is connected to the processor 4, it is unnecessary to readjust the generation timings for the white light image WIA and the fluorescent image FIA and operability is improved. By using any one of the methods explained in the first embodiment, the second embodiment, and the third embodiment for the generation timings for the white light image WIA and the fluorescent image FIA, when fluorescent light emitted from a biological tissue is observed, it is possible to realize a video having a smooth and natural movement.

Note that the output timing of the video signal may be controlled independently from and asynchronously with the generation timings for the white light image WIA and the fluorescent image FIA in the clock control section 48 rather than being controlled in the TV-clock control section 62.

The respective "sections" in the specification are conceptual sections corresponding to the respective functions in the embodiments and do not always correspond to a specific hardware or software routine in a one-to-one relation. Therefore, in the specification, the embodiments were explained assuming virtual circuit blocks (sections) having the respective functions in the embodiments. The respective steps of the respective procedures in the embodiments may be changed in execution order, a plurality of the steps may be simultaneously executed, or the steps may be executed in different order in every execution unless contrary to natures of the steps. Further, all or a part of the respective steps of the respective procedures in the embodiments may be realized by hardware.

The several embodiments of the present invention were explained above. However, the embodiments are presented as examples and are not intended to limit the scope of the invention. The new embodiments can be implemented in other various forms. Various omissions, substitutions, and changes can be made without departing from the gist of the invention. The embodiments and modifications of the embodiments are included in the scope and the gist of the invention and included in the inventions described in claims and the scope of equivalents of the inventions.

What is claimed is:

1. A control apparatus comprising:
   a processor configured to:
      generate a clock at predetermined timing;
      generate a plurality of first white light images of an object based on obtained first signals at timing at which the object is irradiated with white light, based on the generated clock, the generating of the plurality of first white light images comprising generating a first white light image at a first clock, generating a second white light image at a third clock, and generating a third white light image at a fourth clock;
      generate a plurality of fluorescent images of the object based on obtained second signals at timing at which the object is irradiated with excitation light, based on the generated clock, the generating of the plurality of fluorescent images comprising generating a first fluorescent image at a second clock,
      superimpose each of at least the second white light image and the third white light image of the generated plurality of first white light images and the generated first fluorescent image to generate a plurality of first superimposed images, based on the generated clock, the plurality of first superimposed images comprising a first superimposed image superimposing the second white light image and the first fluorescent image at the fourth clock and a second superimposed image superimposing the third white light image and the first fluorescent image at a fifth clock; and subsequent to generating at least the first superimposed image and the second superimposed image, generate a second fluorescent image;

wherein the first clock, the second clock, the third clock, the fourth clock and the fifth clock are sequential.

2. The control apparatus according to claim 1, wherein the processor is further configured to generate a third superimposed image by superimposing, based on the generated clock, the first white light image and the first fluorescent image at the third clock.

3. The control apparatus according to claim 2, wherein the processor is configured to:

continuously a generate the plurality of first white light images based on the generated clock after generating the first fluorescent image at the second clock, a generate the second fluorescent image at a clock timing when the continuous generation of the plurality of first white light images reaches a preset number of times, superimpose, at generation timing for the second fluorescent image, an nth white light image at a point in time when the continuous generation reaches the preset number of times and the first fluorescent image, and superimpose, at a next clock of the generation timing for the second fluorescent image after the present number of times is reached, the nth white light image and the second fluorescent image.

4. The control apparatus according to claim 1, wherein the processor is configured to:

continuously a generate the plurality of first white light images based on the generated clock after generating the first fluorescent image at the second clock, a generate the second florescent image at a clock timing when the continuous generation of the plurality of first white light images reaches a preset number of times, superimpose, at generation timing for the second fluorescent image, an nth white light image at a point in time when the continuous generation reaches the preset number of times and the first fluorescent image, and superimpose the nth white light image and the second fluorescent image after the present number of times is reached.

5. The control apparatus according to claim 1, wherein the predetermined timing is at equal intervals.

6. An endoscope system comprising:

the control apparatus according to claim 1;

a light source configured to irradiate the white light and the excitation light in a time division manner in synchronization with the clock; and an endoscope configured to perform image pickup based on irradiation timing of the light source apparatus and output the first signals and the second signals to the processor.

7. A control method for an endoscope system, comprising:

generating a clock at predetermined timing;

irradiating an object with white light and excitation light in a time division manner in synchronization with the clock;

performing image pickup of the object based on irradiation timing;

generating a plurality of white light images of the object based on first signals obtained at timing at which the object tis irradiated with the white light, based on the generated clock, the generating of the plurality of first white light images comprising generating a first white light image at a first clock, generating a second white light image at a third clock, and generating a third white light image at a fourth clock;

generating a plurality of fluorescent images of the object based on second signals obtained at timing at which the object is irradiated with the excitation light, the generating of the plurality of fluorescent images comprising generating, based on the generated clock, a first fluorescent image at a second clock;

superimposing each of at least the second white light image and the third white light image of the generated plurality of first white light images and the generated first fluorescent image to generate a plurality of first superimposed images, based on the generated clock, the plurality of first superimposed images comprising a first superimposed image superimposing the second white light image and the first fluorescent image at the fourth clock and a second superimposed image superimposing the third white light image and the first fluorescent image at a fifth clock; and subsequent to generating at least the first superimposed image and the second superimposed image, generating a second fluorescent image;

wherein the first clock, the second clock, the third clock, the fourth clock and the fifth clock are sequential.

8. The control method for the endoscope system according to claim 7, further comprising generating a third superimposed image by superimposing, based on the generated clock, the first white light image and the first fluorescent image at the third clock.

9. The control method for the endoscope system according to claim 8, further comprising:

continuously generating the plurality of first white light images based on the generated clock after generating the first fluorescent image at the second clock;

generating the second fluorescent image at a clock timing when the continuous generation of the plurality of first white light images reaches a preset number of times;

superimposing, at generation timing for the second fluorescent image, an nth white light image at a point in time when the continuous generation reaches the preset number of times and the first fluorescent image; and superimposing, at a next clock of the generation timing for the second fluorescent image after the present number of times is reached, the nth white light image and the second fluorescent image.

10. The control method for the endoscope system according to claim 8, further comprising:

converting the generated plurality of first superimposed images into a video signal for displaying the generated plurality of first superimposed images on a predetermined display apparatus;

outputting a predetermined number of frames per unit time period based on an other clock generated;

acquiring, based on the clock earlier than the other clock, the plurality of first white images as many as a number of frames of the video signal outputted per the unit time period;

acquiring, based on the clock earlier than the other clock, the first fluorescent image according to a number of clocks remaining after acquiring the plurality of first white images as many as the number of frames of the video signal within the unit time period; and superimposing the each of plurality of first white images and the first fluorescent image at a same clock as the other clock.

11. The control method for the endoscope system according to claim 7, further comprising:
- continuously generating the plurality of first white light images based on the generated clock after generating the first fluorescent image at the second clock;
- generating the second florescent image at a clock timing when the continuous generation of the plurality of first white light images reaches a preset number of times;
- superimposing, at generation timing for the second fluorescent image, an nth white light image at a point in time when the continuous generation reaches the preset number of times and the first fluorescent image; and
- superimposing the nth white light image and the second fluorescent image after the present number of times is reached.

12. The control method for the endoscope system according to claim 7, further comprising:
- converting the generated plurality of first superimposed images into a video signal for displaying the generated plurality of first superimposed images on a predetermined display apparatus;
- outputting a predetermined number of frames per unit time period based on an other clock generated;
- acquiring, based on the clock earlier than the other clock, the plurality of first white images as many as a number of frames of the video signal outputted per the unit time period;
- acquiring, based on the clock earlier than the other clock, the first fluorescent image according to a number of clocks remaining after acquiring the plurality of first white images as many as the number of frames of the video signal within the unit time period; and
- superimposing the each of plurality of first white images and the first fluorescent image at a same clock as the other clock.

13. The control method for the endoscope system according to claim 7, wherein the predetermined timing is at equal intervals.

* * * * *